United States Patent [19]
Height

[11] 4,010,745
[45] Mar. 8, 1977

[54] FLEXIBLE SPLINT

[76] Inventor: Jack L. Height, 3900 St. Johns Road, Lima, Ohio 45806

[22] Filed: Mar. 4, 1976

[21] Appl. No.: 663,964

[52] U.S. Cl. ............................................ 128/87 R
[51] Int. Cl.² ...................................... A61F 5/04
[58] Field of Search ............. 128/87 R, 83, 84, 92, 128/77, 89, 90, 88, 80; 3/19

[56] References Cited
UNITED STATES PATENTS

| | | | |
|---|---|---|---|
| 2,500,622 | 3/1950 | Aho | 3/19 |
| 2,767,708 | 10/1956 | Keropian | 128/77 |
| 3,846,846 | 11/1974 | Fischer | 128/92 BB |
| 3,970,305 | 7/1976 | Hawkins | 128/87 R |

Primary Examiner—John D. Yasko
Attorney, Agent, or Firm—James A. Eyster

[57] ABSTRACT

The splint has two modes of adjustment, flexible and rigid. It consists of a plurality of similar pads strung on a flexible wire. Friction elements are provided between pads. A take-up screw is provided at one end of the wire and a take-up eccentric at the other, permitting the friction elements to be adjusted to any desired degree of low friction between pads, or adjusted to such high friction as to lock the pads together. In another embodiment both the take-up screw and the take-up eccentric are at the same end of the flexible splint.

12 Claims, 10 Drawing Figures

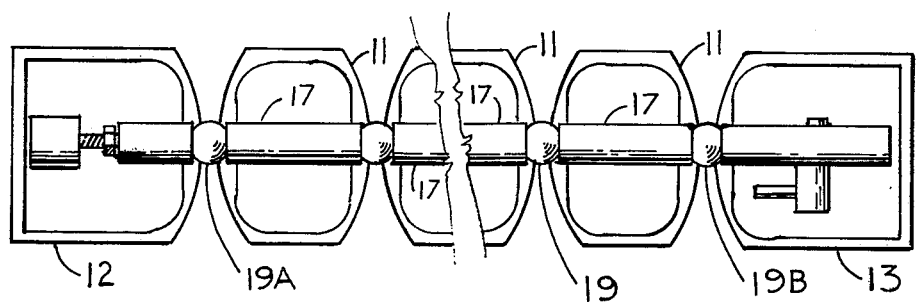
FIG. 1
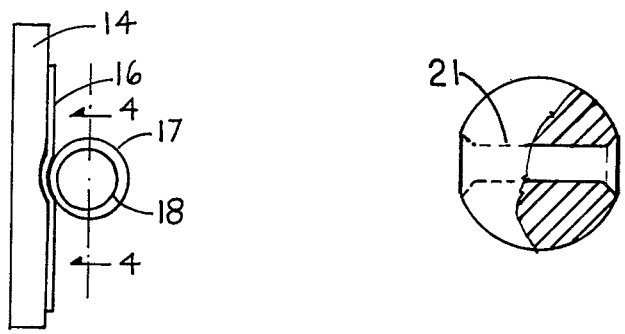
FIG. 2
FIG. 3
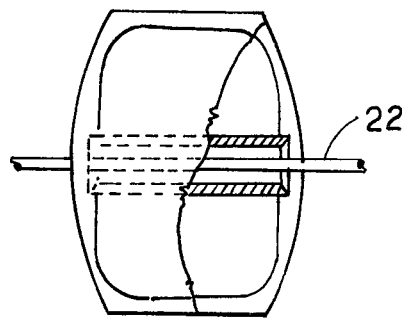
FIG. 4

FLEXIBLE SPLINT

BACKGROUND OF THE INVENTION

1. Field of the Invention

This invention relates to rigid elements for positioning on a broken limb of a human or animal body to keep the limb immobile or for use in keeping a part of the body in a fixed position.

2. Description of the Prior Art

When a limb or digit is broken it is highly desirable to splint it immediately to prevent further damage to the ends of the broken bone or to the muscles, ligaments or blood vesels. After such immobilization the patient can then be moved with relative safety to a hospital. The rigid element used to splint the injured part must usually be improvised and may be a board, cane, bar, or even an umbrella. If splining is done by an ambulance attendant, rigid splints made for the purpose such as molded plastic splints may be used.

After a bone has been set by the surgeon he generally applies a plaster cast which stays on until the bone has knit. However, if the bone has been pinned after setting, the case, after several days is split longitudinally and temporarily removed so that the patient can get some exercise. This is highly desirable to prevent the formation of thrombi.

SUMMARY OF THE INVENTION

The flexible splint consists of a number of pads strung in a line on a series of tubes. These tubes are separated by ball joints and connected by a flexible steel wire. This wire can be loosened to allow the pads to move relative to one another, or tightened to bond the pads into a single, rigid unit.

One object of this invention is to provide a splint which at will can be made completely flexible or completely rigid.

Another object is to provide a series of pads strung on a wire to form a splint. In a first position of adjustment of the wire the pads are all movable relative to each other, so that when laid along a broken limb the splin can conform to the shape of the injured limb. In a second mode of use, after positioning the splint to become rigid, with no possible movement of the pads relative to each other.

BRIEF DESCRIPTION OF THE DRAWINGS

FIG. 1 depicts the stiffening layer side of one embodiment of the flexible splint.

FIG. 2 is an edge view of one of the intermedite pads.

FIG. 3 is an enlarged view of one of the balls separating the pads.

FIG. 4 is an enlarged view of the stiffener side of one of the intermediate pads, with the tube partly in section on line 4 — 4, FIG. 2.

DESCRIPTION OF THE PREFERRED EMBODIMENT

Figure 5:
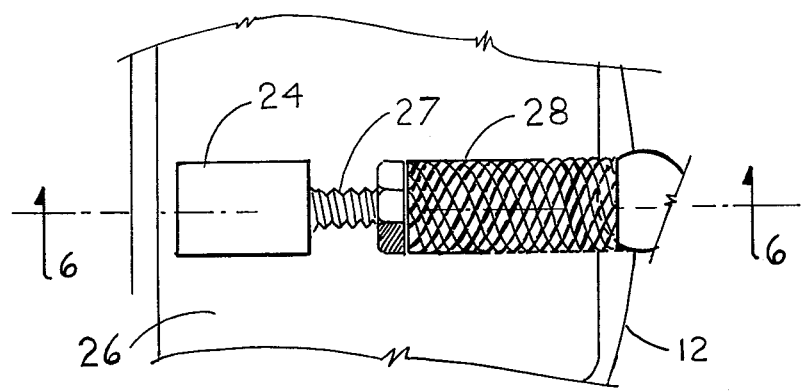
FIG. 5 is an enlarged view of the stiffener side of end pad 12.

Referring to FIG. 1, the flexible splint comprises identical intermediate pads 11, end pad 12 and a second similar but not identical end pad 13. Each pad comprises a padding layer as shown in FIG. 2 at 14, and a stiffening layer or stiffener 16.

The padding layer 14 may be made, for example of foam rubber or jute, and can be covered with vinyl or other protective material. Its thickness, length and width will depend on whether the flexible splint will be used on a person or an animal, and on the size of the limb, digit or some other part which is to be splinted.

The stiffener has exterior dimensions slightly smaller than those of the padding layer so as not to come in contact with the body of the patient. The thickness and material of the stiffener are such as to provide strength and stiffness combined with lightness.

The padding is secured to the stiffener by an adhesive.

With each pad stiffener there is associated a tube at 17, FIGS. 1 and 2, having a circular bore or internal cross section. In this embodiment the external cross section is also circular. These tubes are tightly fastened to the stiffener in the intermediate pads and in one end pad, 13. All tube bores may have the same diameter as shown at 18, FIG. 2. Each of the intermediate pad tubes is flared or bevelled at both ends and the end tubes are flared or bevelled at one end, all flares being preferably sized to fit identical spherical balls 19, FIGS. 1 and 3. The balls separate the pads and are made, for example, of steel, bronze or plastic. Each ball has a diametral hole 21. A connecting element, which may be stranded steel cable 22, FIG. 4, passes through all tubes and balls and is secured in both end pads. In at least one end pad the cable is secured adjustably, and in this embodiment the cable is secured adjustably in both end pads.

Figure 6:
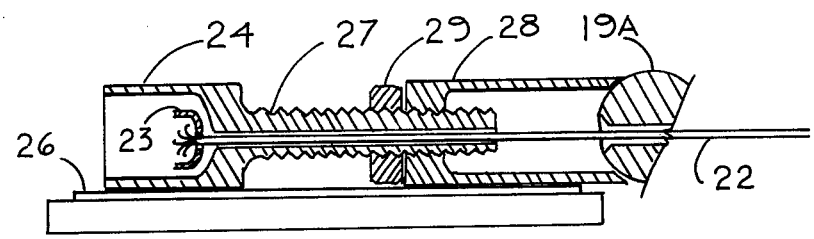
FIG. 6 is an edge view of end pad 12 sectioned on the line 6 — 6, FIG. 5.

End pad 12, depicted in FIGS. 5 and 6, adjustably anchors one end of the cable 22 while permitting cable rotation, and provides a micrometer screw adjustment of the cable length, thus providing close adjustment of the friction between each tube and the adjacent balls throughout the entire length of the flexible splint. The cable 22 passes through a center hole in housing 24 and the cable end is secured, for example by soldering, in a cable retainer 23. The housing 24 is securely fastened to the stiffener 26 of pad 12. The housing 24 has a threaded cylindrical extension 27 which mates with a female thread in the end of tube 28. This tube 28 is flared or chamfered at the end opposite to its threaded end and abuts the adjacent ball 19A. The outside surface of tube 28 is knurled. A lockout 29 is provided to lock the thread motion, or a fine thread may be employed instead.

Figures 7, 8:
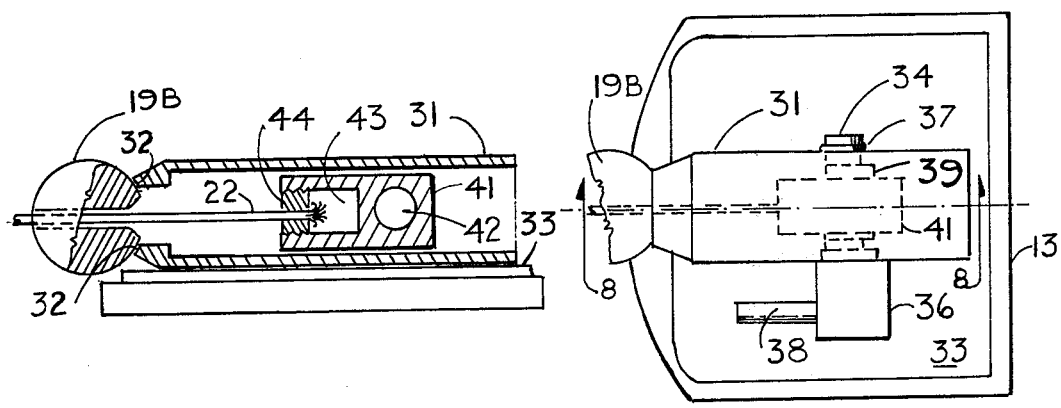
FIG. 7 depicts the stiffener face of end pad 13.
FIG. 8 depicts an edge view of end pad 13 partially sectioned on the 45 line 8 — 8, FIG. 7.

The end pad 13 is shown in detail in FIGS. 7 and 8, providing an eccentric mechanism for tightening cable 22 in order to convert friction contacts between balls and tubes to locking contacts. An eccentric housing or tube, 31, has the same flare dimension at one end, 32, as have the other tubes and makes contact with a ball 19B identical with the other balls. Tube 31 is securely fastened to the stiffener 33 of pad 13. A shaft 34 is borne in bearings in the tube 31, carrying a boss 36 at one end and held by retainer ring 37 at the other. A handle or lever 38 is fastened to the boss. The middle part of shaft 34 is enlarged to form an eccentric 39; an eccentric follower 41 is provided with a hole 42 fitting the eccentric 39. One end of follower 41 has a cavity 43 threaded at its open end. A threaded disc 44 is screwed therein. This disc 44 has a center hole through which the cable 22 is pressed. In assembly, the disc is removed, fitted on the end of the cable and secured thereon by soldering or otherwise. The disc is then screwed into the fastener 41 and secured by pinning, staking or otherwise. The follower is then inserted in tube 31 and the shaft 34 is put into its bearings and through hole 42 in follower 41, and secured by ring 37.

In operation of this embodiment of the flexible splint, normally the eccentric 39 will be positioned on its loosened cable position and the screw 27 of pad 12 will be in such position as to exert a slight pull on the cable. The several pads of the splint will thereby be pulled together so that each joint between a ball and an adjacent tube will have some friction. Tension of the cable 22 is adjusted by turning tube 28 until the friction between balls and tubes are sufficient to hold all parts of the splint in any attitude, yet not so must as to prevent easily forcing the splint into another altitude.

In applying the splint so adjusted to a broken limb the splint is conformed to the limb and tied thereto, for example by an elastic bandage or by a fabric having hooked filaments which adhere on contact. After applying the splint the handle or lever 38 is turned so that the eccentic 39 is rotated 180° to the position shown in FIG. 7. This tightens cable 22 to such an extend that all the bearings between tube and ball are immovably locked into position; thus the flexible splint becomes inflexible and holds the injured limb in the set position.

In another use of this invention the flexible splint replaces the plaster case which, in present practise, is applied after a broken limb is set. This application of the invention greatly facilitates the later temporary removal of the splint to allow the patient to exercise.

In a second embodiment both the screw adjustment and the eccentric adjustent of the cable tension are on the same end of the flexible splint. This embodiment is depicted in FIGS. 9 and 10.

Figure 9:
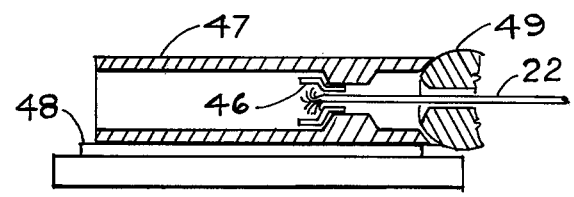
FIG. 9 depicts a side view of an end pad providing a non-adjustable anchorage for one end of the cable.
Figure 10:
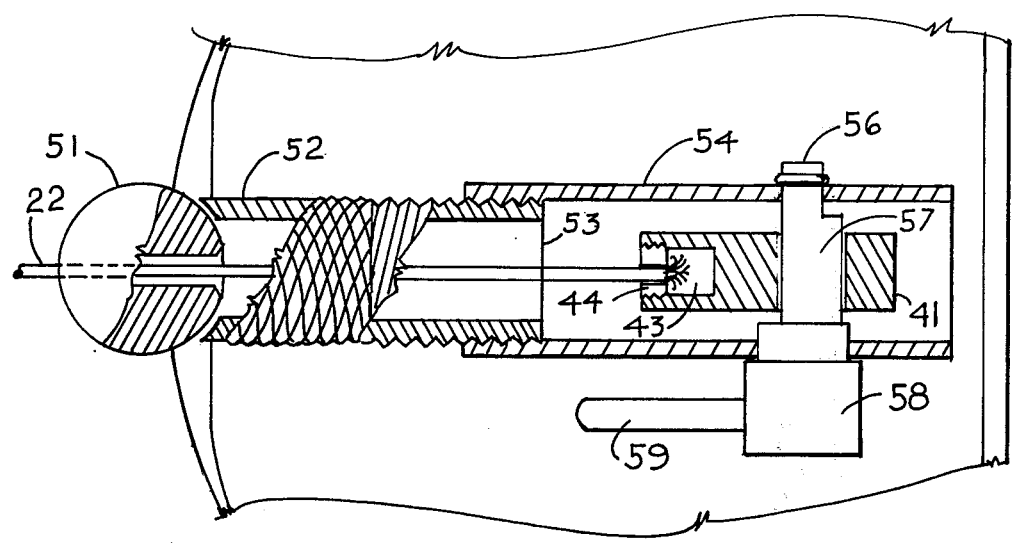
FIG. 10 depicts an end pad providing a cable anchorage having both screw and eccentric adjustments of cable tension.

In FIG. 9 one end of cable 22 is non-adjustably secured in a cable retainer 46 loosely fitted into a cable retainer housing 47, which is fastened to an end pad stiffener 48. One end of the housing 47 abuts a ball 49. The other end of the cable 22 is anchored at the other end pad as shown in FIG. 10. The cable, after passing through ball 51, passes through a knurled tube 52 abutting the ball, the tube carrying threads on one end 53. These threads are preferably fine so as to stay at any adjustment without requiring a locknut. The threads engage female threads in a tube 54 secured to the stiffener of the end pad. This tube 54 carries a cross shaft 56 which has a central eccentric portion 57 and an end boss 58 bearing a crank handle 59. An eccentric follower 41 surrounds the eccentric 57, and at one end is provide with a cavity 43 and a disc 44 threaded therein. The end of cable 22 passes through disc 44 and is secured thereto.

In operation, the eccentric handle is put in its loose position and the tube 52 is adjusted by screwing into tube 54 until the tension cable 22 produces slight friction at each ball joint, so that the flexible splint will stay in any position. The splint is then applied to the broken limb and the eccentric lever is moved to turn the eccentric 57 by 180° to the position shown in FIG. 10, locking the splint rigidly.

I claim:

1. A flexible splint comprising:
   a plurality of similar pads, positioned in a line in a single series;
   connecting means comprising a cable connecting all said pads with each other;
   friction means comprising tubes and balls separating each said pad from its adjacent pads; and
   adjusting means for adjusting the tension of said cable, whereby said adjusting means controls the degree of friction of said friction means.

2. A flexible splint in accordance with claim 1 in which said pads comprise at least one intermediate pad and first and second end pads, each said pad having a soft padded side and a stiffener side.

3. A flexible splint in accordance with claim 1 in which said friction means comprises:
   a plurality of tubes having the same selected internal diameter and the same selected internal circular cross section, each said tube being associated with one particular pad; and
   a plurality of spherical balls in number one less than the number of said plurality of tubes, each said ball having a diametral hole, the diameters of said balls being greater than the selected diameter of said tubes, said balls being positioned each between two said tubes.

4. A flexible splint in accordance with claim 3, in which said connecting means comprises a cable passing through said plurality of tubes and plurality of balls, tubes and balls being in alternation, said cable terminating in first and second end pads.

5. A flexible splint in accordance with claim 1 in which said adjusting means comprises screw tensioning means for continously adjusting the friction of said friction means by adjusting the tension on said cable.

6. A flexible splint in accordance with claim 5 in which said screw tensioning means comprises:
   A first member secured to one said end pad, said member being also secured to one end of said cable; and
   A rotatable first tube member threadedly connected to said first member and abutting one of said balls, whereby the tension of said cable can be adjusted.

7. A flexible splint in accordance with claim 1, in which said adjusting means comprises eccentric tensioning means for adjusting in at least one step the friction of said friction means by adjusting the tension on said cable.

8. A flexible splint in accordance with claim 7 in which said eccentric tensioning means comprises:
   A second tube member abutting one of said balls;
   A follower inside said second tube member secured to one end of said cable, said follower having a transverse hole; and
   A shaft having an eccentric middle portion, said shaft being journalled in transverse being holes in said second tube member, said shaft eccentric portion being borne in the transverse hole in said follower, said shaft being provided with a handle.

9. A flexible splint in accordance with claim 1 comprising:
   A plurality of pads including at least one intermediate pad, a first end pad and a second end pad, each pad having a padded side and a stiffener side;
   A plurality of tubes, each said tube being associated with each one of said pads, all said tubes having the same selected internal circular shape and the same internal diameter;

A plurality of spherical balls equal in number to one less than the number of said tubes, each said ball having a diameter greater than said internal diameter, each said ball being pierced by a diametral hole, each said ball being positioned abutting the ends of two said tubes whereby said tubes and balls in alternation form a continuous unbroken series;

A cable having tensile strength passing through said unbroken series and terminating in the tube associated wth said first end pad and in the tube associated with said second end pad; and Tension means in at least one of said end pads for applying tension to said cable.

10. A flexible splint in accordance with claim 9 in which said tension means comprises:

A hollow member secured to said first end pad stiffener side, said hollow member having a male threaded projection, said hollow member having a central hole whereby said cable may be threaded therethrough and rotatably secured; and A first tube member of circular internal cross section having one end provided with a female thread mating with said male threaded projection and having the other end abutting one said ball.

11. A flexible splint in accordance with claim 9 in which said tension means comprises:

A second tube member having one end of circular internal cross section and abutting one of said balls;

A follower having in one end a cavity provided with a female thread, and having a transverse circular cross section hole in the other end;

A disc having a center hole for reception and securing of one end of said cable and having a male thread on its edge mating with said cavity female thread;

A shaft bearing an eccentric portion, said shaft borne by transverse bearings in said second tube member, said eccentric portion being borne by the transverse hole in said follower; and a handle fastened to said shaft.

12. A flexible splint in accordance with claim 4 in which said adjusting means comprises combined first and second elements both embodied in only one of said first and second pads, said combined first and second elements comprising;

A third tube secured to one said end pad, said third tube having one end bearing an internal thread, said third tube bearing a cross shaft having an eccentric portion and having a crank handle;

An eccentric follower on cross shaft eccentric portion; Means securing one end of said cable in said eccentric follower; and A fourth tube engaging at one end said internal thread and at the other end abutting one of said balls, whereby the tension of said cable is adjustable by said internal thread and also by said eccentric portion.

* * * * *